(12) United States Patent
Nietfeld

(10) Patent No.: US 7,706,983 B2
(45) Date of Patent: Apr. 27, 2010

(54) METHOD FOR ANONYMOUSLY REGISTERING, STORING AND USING BODY MATERIAL AND/OR INFORMATION DERIVED THEREFROM

(75) Inventor: Jan Jaap Nietfeld, Ke Maarsen (NL)

(73) Assignee: Intresco B.V. (NL)

( * ) Notice: Subject to any disclaimer, the term of this patent is extended or adjusted under 35 U.S.C. 154(b) by 265 days.

(21) Appl. No.: 10/204,817

(22) PCT Filed: Feb. 26, 2001

(86) PCT No.: PCT/NL01/00160

§ 371 (c)(1),
(2), (4) Date: Dec. 6, 2002

(87) PCT Pub. No.: WO01/70023

PCT Pub. Date: Sep. 27, 2001

(65) Prior Publication Data

US 2003/0108905 A1     Jun. 12, 2003

(30) Foreign Application Priority Data

Feb. 25, 2000   (NL) .................................. 1014491

(51) Int. Cl.
*G01N 33/48* (2006.01)
(52) U.S. Cl. ...................................................... 702/19
(58) Field of Classification Search .................. 702/19, 702/20
See application file for complete search history.

(56) References Cited

U.S. PATENT DOCUMENTS 4,880,750 A * 11/1989 Francoeur ................... 436/501
5,876,926 A * 3/1999 Beecham ........................ 435/5

FOREIGN PATENT DOCUMENTS

| WO | WO 91 09521 A | 7/1991 |
| WO | WO 95 15493 A | 6/1995 |
| WO | WO 97 43453 A | 11/1997 |

OTHER PUBLICATIONS

Service, Robert. "Tapping DNA for Structures Produces a Trickle," Science (2002) vol. 298, pp. 948-950.*
Kirby, Lorne, DNA Fingerprinting: An Introduction, W.H. Freeman and Company: New York 1992, pp. 1-5, 35-75, 117-121, 124-127, 180, 181, 189-215, 284 and 285.*

* cited by examiner

*Primary Examiner*—Jerry Lin
(74) *Attorney, Agent, or Firm*—Wood, Phillips, Katz, Clark & Mortimer

(57) ABSTRACT

The present invention relates to a method for anonymously registering, storing and using body material of an individual, and/or information derived from the body material, wherein the anonymity can only be removed with the assistance of the individual himself, comprising the following steps, to be performed in suitable sequence, of: (a) collecting the body material of the individual; (b) determining a distinguishing biological characteristic of the body material; (c) linking the distinguishing biological characteristic to the body material by means of an anonymous coding system; (d) optionally using the body material for the purpose of obtaining information; (e) storing the body material and/or the information derived therefrom; and (f) if desired, returning the body material and/or making the information derived therefrom available to the individual only after a biological characteristic of the individual corresponding with the biological characteristic of the body material has been determined, and it has been established that the biological characteristic of the individual is identical to the biological characteristic of the body material.

6 Claims, No Drawings

METHOD FOR ANONYMOUSLY REGISTERING, STORING AND USING BODY MATERIAL AND/OR INFORMATION DERIVED THEREFROM

BACKGROUND OF THE INVENTION

1. Field of the Invention

The present invention relates to a method for anonymously registering, storing and using body material of an individual, and/or the information derived from the body material.

2. Description of the Prior Art

Owing to the rapidly progressing developments in medical science and biotechnology, use is increasingly being made of the storage for a shorter or longer time of diverse types of body material of people. The stored body material can for instance be used to derive information therefrom at some point in time for the benefit of the person himself, or for medical science and/or biotechnology in general. Storage of body material for a longer period may for instance be desired to create the possibility of being able to utilize the material at a later stage, for instance in order to treat the individual. In addition to storing stem cells from blood from the umbilical cord, it is possible to further envisage the storage of sperm cells, egg cells, embryonic cells and/or bone marrow cells.

In addition to the requirements set in the medical-biological field regarding handling and storage of cells and/or tissues in respect of quality and safety, there are generally also set requirements regarding the management of the personal data of the depositors of the body material, so that the confidentiality of the medical and biological data obtained during testing of and/or treatments with/of the body material can be guaranteed. The registration, storage and the use of non-anonymous material and non-anonymous data are thus subject to legal limitations, since ethical and judicial problems could otherwise result. Non-anonymous data could for instance result in discrimination of the depositors by employers, insurance companies and/or other bodies. Not only does such a system of non-anonymous data have the above stated limitations, the management and the responsibility for protecting personal details moreover lies with the registering body without the depositors being able to exert any direct influence or make checks thereon. It therefore occurs that in some cases the body material and/or the data obtained therewith are registered, stored and/or used anonymously, i.e. such that no connection can be made to the person from which the body material originates, and whose personal data is thus no longer retrievable. This has the drawback however that the material and the data obtained therewith could never be made available again to the relevant person from whom the material originates.

SUMMARY OF THE INVENTION

The object of the present invention is to obviate the above stated drawback.

This object is achieved by the invention by providing a method for anonymously registering, storing and using body material of an individual, and/or information derived from the body material, wherein the anonymity can only be removed with the assistance of the individual himself, comprising the following steps, to be performed in suitable sequence, of:

(a) collecting the body material of the individual;

(b) determining a distinguishing biological characteristic of the body material;

(c) linking the distinguishing biological characteristic to the body material by means of an anonymous coding system;

(d) optionally using the body material for the purpose of obtaining information;

(e) storing the body material and/or the information derived therefrom; and (f) if desired, returning the body material and/or making the information derived therefrom available to the individual only after a biological characteristic of the individual corresponding with the biological characteristic of the body material has been determined, and it has been established that the biological characteristic of the individual is identical to the biological characteristic of the body material.

DETAILED DESCRIPTION OF THE PREFERRED EMBODIMENTS

The present invention therefore provides a method for on the one hand registering, storing and using body material of an individual and/or information derived therefrom strictly anonymously, i.e. so as to be not retrievable by third parties, while on the other hand the option remains open to the relevant individual from whom the body material originates to remove the anonymity so that the stored material can once again be made available to the individual at any desired point in time and/or the individual can obtain access to the data obtained therewith at any desired moment. The decision to make the identification required for this purpose can herein be made only with the assistance of the individual, the depositor, himself. Without the co-operation of the depositor the material and/or the information will therefore remain anonymous.

The registration, storage and use of the body material and the data obtained therewith thus takes place according to the invention without registration of personal data, but by means of an anonymous biological coding system, only the depositor of which possesses the biological key to identification.

According to the invention, when cells and/or tissue are taken/obtained from the individual, the material is provided with an anonymous code. The code can for instance consist of numbers, and/or letters, and/or other symbols, such as for instance a bar code or a matrix code. The body material is for instance transported under this anonymous code to the cell/tissue bank, where the material is registered under the assigned anonymous code. A unique distinguishing biological characteristic (for instance a DNA-fingerprint) of the anonymous material is then determined, and this distinguishing biological characteristic is linked to the assigned anonymous code in a secured databank. Under this anonymous code the material is (if necessary) made suitable for storage and/or use for research. The body material is thus only known under the assigned anonymous code when the body material is made suitable for and actually stored in the storage facility and/or during research. The storage and use of the medical and/or biological data obtained by the research also takes place solely under the assigned anonymous code.

To enable recovery of the stored material, or to enable access to the data obtained using the material, the depositor must provide the biological key to identification in the form of an individual distinguishing biological characteristic such as has been previously determined for the body material of the depositor (for instance the DNA-fingerprint). The identification takes place by determining which distinguishing biological characteristic in the secured databank of the cell/tissue bank is identical to the biological key provided by the depositor. After positive identification the stored material can be returned or access can be granted to the data registered under the associated anonymous code. The body material and/or the information derived therefrom can be used for the benefit of the relevant individual himself, but for instance also for the benefit of other individuals (for instance relatives), or of groups in society, or society as a whole, by using or allowing the material and/or the information derived therefrom to be used for/in medical treatments and/or research.

The biological characteristic is preferably a DNA-fingerprint. With a DNA-fingerprint a unique distinguishing biological characteristic can be obtained such that the provided material and/or the information derived therefrom can once again be made available to the correct person. A DNA-fingerprint can for instance be made using standard molecular biological techniques, which are known to the skilled person.

In another embodiment of the method according to the invention the biological characteristic comprises a specific pattern of molecules present in the body material. The specific pattern preferably comprises a specific arithmetical ratio of numbers of molecules in the biological material originating from two or more types of molecule such as for instance proteins, carbohydrates, glycoproteins, proteoglycans, lipids, lipoproteins, glycolipids and nucleotides.

A subsequent suitable embodiment of the method is obtained when the biological characteristic comprises a specific three-dimensional structure of one or more of the above stated types of molecule present in the body material, particularly the three-dimensional structure of one or more supramolecular assemblies of two or more of the molecules.

In a further particular embodiment the biological characteristic comprises a combination of a specific pattern and/or a specific three-dimensional structure of one or more of the types of molecule present in the body material. In this manner the reliability of the identification system by means of the biological characteristic can be further increased.

For the identification use is made of the distinguishing biological characteristic of the individual and the data of the anonymous coding system. The anonymous coding system preferably consists of an anonymous distinguishing symbol linked to the body material, in particular a number and/or letter code, a bar code, or a matrix code, wherein the distinguishing biological characteristic of the body material stored in a secured databank is linked to the same anonymous distinguishing symbol. It is hereby not possible to find out from which individual the body material originates without the relevant individual giving his or her consent and/or cooperation.

According to the invention the body material can comprise any biological material originating from an individual, including body cells, such as stem cells, and/or tissues, such as for instance skin.

The information derived from the body material can for instance consist of diagnostic data, or data obtained on the basis of medical and/or biotechnological research. The data can be based on the body material of a single individual and/or a group of individuals and/or obtained by bio-statistical processing of the data originating from the body material of one or more groups of individuals.

The invention claimed is:

1. A method for anonymously registering, storing and using a sample of body material of a depositor and/or information derived from the sample of body material, wherein access to the sample and/or the information derived from the sample can be given to the depositor only after he/she has provided a biological key, comprising the steps of:
   (a) submitting a sample of body material of the depositor to a cell/tissue bank;
   (b) registering said sample of body material under an anonymous code;
   (c) using said sample of body material for deriving information:
      i) by determination of a biological characteristic of the sample of body material that distinguishes individuals or;
      ii) by determination of a biological characteristic of the sample of body material that distinguishes individuals and deriving data from the sample of body material, other than said biological characteristic that distinguishes individuals, wherein the data are selected from the group consisting of diagnostic data, medical data, biological data, medical research data, and biotechnological research data;
   d) storing said sample of body material and/or said data under said anonymous code and linking said biological characteristic to said sample of body material and/or said data via the anonymous code in a secured databank; and
   e) recovering the stored sample of body material and/or said data derived from the sample of body material, and giving access to said recovered sample and/or data by the consent of the depositor for purposes chosen from the group consisting of medical treatment, research, and diagnostics, after the depositor of the sample provides a biological key in the form of a depositor biological characteristic that is identical with said biological characteristic of said sample of body material,
   i) when the depositor remains anonymous, or
   ii) when the depositor identifies him/herself.

2. The method as claimed in claim 1, wherein the biological characteristic comprises a DNA-fingerprint.

3. The method as claimed in claim 1, wherein the biological characteristic comprises a pattern of types of molecules present in the body material.

4. The method as claimed in claim 3, wherein the pattern comprises an arithmetical ratio of numbers of molecules originating from two or more types of molecules present in the body material.

5. The method as claimed in claim 3, wherein the types of molecules are chosen from the group consisting of proteins, carbohydrates, glycoproteins, proteoglycans, lipids, lipoproteins, glycolipids and nucleotides.

6. The method of claim 1, wherein the anonymous code is selected from the group consisting of a number code, a letter code, a number and letter code, a bar code, and a matrix code.

* * * * *